(12) United States Patent
Shen et al.

(10) Patent No.: US 9,863,870 B2
(45) Date of Patent: Jan. 9, 2018

(54) METHOD AND APPARATUS TO USE MULTIPLE SPECTROSCOPIC ENVELOPES TO DETERMINE COMPONENTS WITH GREATER ACCURACY AND DYNAMIC RANGE

(75) Inventors: Jing Shen, Houston, TX (US); Christopher Michael Jones, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 91 days.

(21) Appl. No.: 13/984,813

(22) PCT Filed: Feb. 11, 2011

(86) PCT No.: PCT/US2011/024633
§ 371 (c)(1),
(2), (4) Date: Sep. 26, 2013

(87) PCT Pub. No.: WO2012/108886
PCT Pub. Date: Aug. 16, 2012

(65) Prior Publication Data
US 2014/0042323 A1 Feb. 13, 2014

(51) Int. Cl.
*G01J 5/02* (2006.01)
*G01N 21/25* (2006.01)
(Continued)

(52) U.S. Cl.
CPC ......... *G01N 21/255* (2013.01); *E21B 47/102* (2013.01); *E21B 49/08* (2013.01);
(Continued)

(58) Field of Classification Search
CPC .................................................. G01N 21/255
(Continued)

(56) References Cited

U.S. PATENT DOCUMENTS 4,567,366 A * 1/1986 Shinohara ............ G01N 21/255
250/339.13
5,791,497 A * 8/1998 Campbell et al. ............ 209/577
(Continued)

OTHER PUBLICATIONS

PCT International Search Report and Written Opinion dated Apr. 14, 2011, in related International Application No. PCT/US2011/024633, 7 pages.

(Continued)

*Primary Examiner* — David Porta
*Assistant Examiner* — Abra Fein
(74) *Attorney, Agent, or Firm* — Haynes and Boone, LLP

(57) ABSTRACT

A method of using spectroscopic envelopes for determining components in a sample may include selecting spectroscopic envelopes and passing input light through a sample comprising at least one absorbing component is provided. The method includes measuring throughput light with a photo-detector and determining the concentration of the at least one absorbing component in the sample using the measured throughput, wherein at least one of the plurality of spectroscopic envelopes overlaps at least one absorption band of the at least one absorbing component in the sample. An apparatus for determining components in a sample including an input light source having a spectrum and a sample container having a fixed optical path-length is also provided. The apparatus may include a plurality of pre-selected spectroscopic envelopes to select spectral portions of the throughput light from the sample; and at least one photo-detector to measure the throughput light selected by the spectroscopic envelopes.

19 Claims, 8 Drawing Sheets

(51) Int. Cl.
  *E21B 47/10* (2012.01)
  *E21B 49/08* (2006.01)
  *G01N 33/28* (2006.01)
  *G01N 21/3577* (2014.01)
  *G01N 21/359* (2014.01)

(52) U.S. Cl.
  CPC ....... *G01N 33/2823* (2013.01); *G01N 21/359* (2013.01); *G01N 21/3577* (2013.01); *G01N 2201/129* (2013.01)

(58) Field of Classification Search
  USPC .................................................. 250/339.12
  See application file for complete search history.

(56) References Cited

U.S. PATENT DOCUMENTS

| | | | |
|---|---|---|---|
| 5,822,058 A * | 10/1998 | Adler-Golden | G01N 21/359 356/300 |
| 5,939,717 A | 8/1999 | Mullins | |
| 6,437,326 B1 | 8/2002 | Yamate et al. | |
| 7,173,239 B2 | 2/2007 | DiFoggio | |
| 2005/0018192 A1 | 1/2005 | DiFoggio et al. | |
| 2007/0035737 A1 | 2/2007 | Andrews et al. | |
| 2007/0137292 A1 | 7/2007 | Xian et al. | |
| 2007/0201136 A1 | 8/2007 | Myrick et al. | |
| 2007/0291251 A1* | 12/2007 | Rensen et al. | 356/39 |
| 2008/0111064 A1 | 5/2008 | Andrews et al. | |
| 2008/0196582 A1* | 8/2008 | Tjeenk Willink et al. | 95/57 |
| 2009/0299946 A1 | 12/2009 | Myrick et al. | |
| 2010/0211329 A1 | 8/2010 | Farquharson et al. | |

OTHER PUBLICATIONS

Mullins et al. "Gas-Oil Ratio of Live Crude Oils Determined by Near-Infrared Spectroscopy;" Appl. Spectrosc. 55(2), pp. 197-201.
International Preliminary Report on Patentability and the Written Opinion dated Aug. 22, 2013, in related International Application No. PCT/US2011/024633.

* cited by examiner

METHOD AND APPARATUS TO USE MULTIPLE SPECTROSCOPIC ENVELOPES TO DETERMINE COMPONENTS WITH GREATER ACCURACY AND DYNAMIC RANGE

BACKGROUND

1. Technical Field

Embodiments disclosed herein relate generally to the field of near infrared measurement of absorbing components in a sample. More particularly, embodiments disclosed herein are related to measurement of Gas-Oil Ratio (GOR) for crude oil extraction.

2. Description of Related Art

The Gas-Oil Ratio (GOR) is an important parameter for practical purposes in oil extraction environments. GOR is a volumetric measure providing the ratio of gas to oil at atmospheric pressures, once the liquid is extracted from the "downhole" at high pressures. The GOR is conventionally defined as the volume of gas at standard conditions such as standard temperature and pressure conditions, in cubic feet divided by the number of stock tank barrels of oil (each stock tank barrel equal to 42 gallons). Stock tank refers to liquid at the surface, and not barrels of fluid at the reservoir. An inherent relation exists between GOR and the mass percentage of methane $CH_4$ in the liquid at the downhole. A procedure to obtain GOR may be approximated by such methods described according to Mullins et al. "Gas-Oil Ratio of Live Crude Oils Determined by Near-Infrared Spectroscopy;" Appl. Spectrosc. 55(2) pp. 197-201. The relation between GOR and $CH_4$ concentration in the downhole is valid for most crude oil samples having relatively low concentrations of $H_2S$ or $CO_2$. Therefore, it is of practical importance to accurately measure $CH_4$ dissolved in the liquid phase of the crude sample at the downhole.

Near-infrared (NIR) absorption spectroscopy has been used to estimate the GOR. Applications of NIR spectroscopy use one spectroscopic envelope located between 1620 and 1700 nm to estimate the GOR. Two absorption bands have been detected for $CH_4$, one centered at 1670 nm, and one centered at 1682 nm. Also, there is knowledge of a $CO_2$ absorption band centered at approximately 2010 nm. This has limited applications of NIR for measuring GOR to wavelengths below 2000 nm.

What is needed is a method to reliably determine components in a sample using broad-band absorption spectroscopy. More specifically, what is needed is a method to reliably determine GOR using broad band absorption spectroscopy.

SUMMARY

According to embodiments disclosed herein, a method of using spectroscopic envelopes for determining components in a sample may include the steps of selecting a plurality of spectroscopic envelopes and passing input light through a sample comprising at least one absorbing component. Further, the method may include measuring throughput light from the sample with a photo-detector and determining the concentration of the at least one absorbing component in the sample using the measured throughput, wherein at least one of the plurality of spectroscopic envelopes overlaps at least one absorption band of the at least one absorbing component in the sample.

According to some embodiments disclosed herein, an apparatus for determining components in a sample may include an input light source having a spectrum, and a sample container having a fixed optical path-length wherein the input light passes through a sample in the sample container forming a throughput light, the sample having at least one absorbing component. The apparatus may also include a plurality of pre-selected spectroscopic envelopes to select spectral portions of the throughput light from the sample; and at least one photo-detector to measure the throughput light selected by the spectroscopic envelopes. Further, the apparatus may include an analyzer to use the measurement from the photo-detectors to determine the concentration of the at least one absorbing component in the sample.

These and other embodiments will be described in further detail below, with reference to the following drawings.

BRIEF DESCRIPTION OF THE DRAWINGS

FIG. 2b shows a spectroscopic envelope for incoming light and throughput light according to embodiments consistent with FIG. 2a.

Wherever possible, the same reference numbers are used throughout the drawings to refer to the same or like elements.

DETAILED DESCRIPTION

Figure 1:
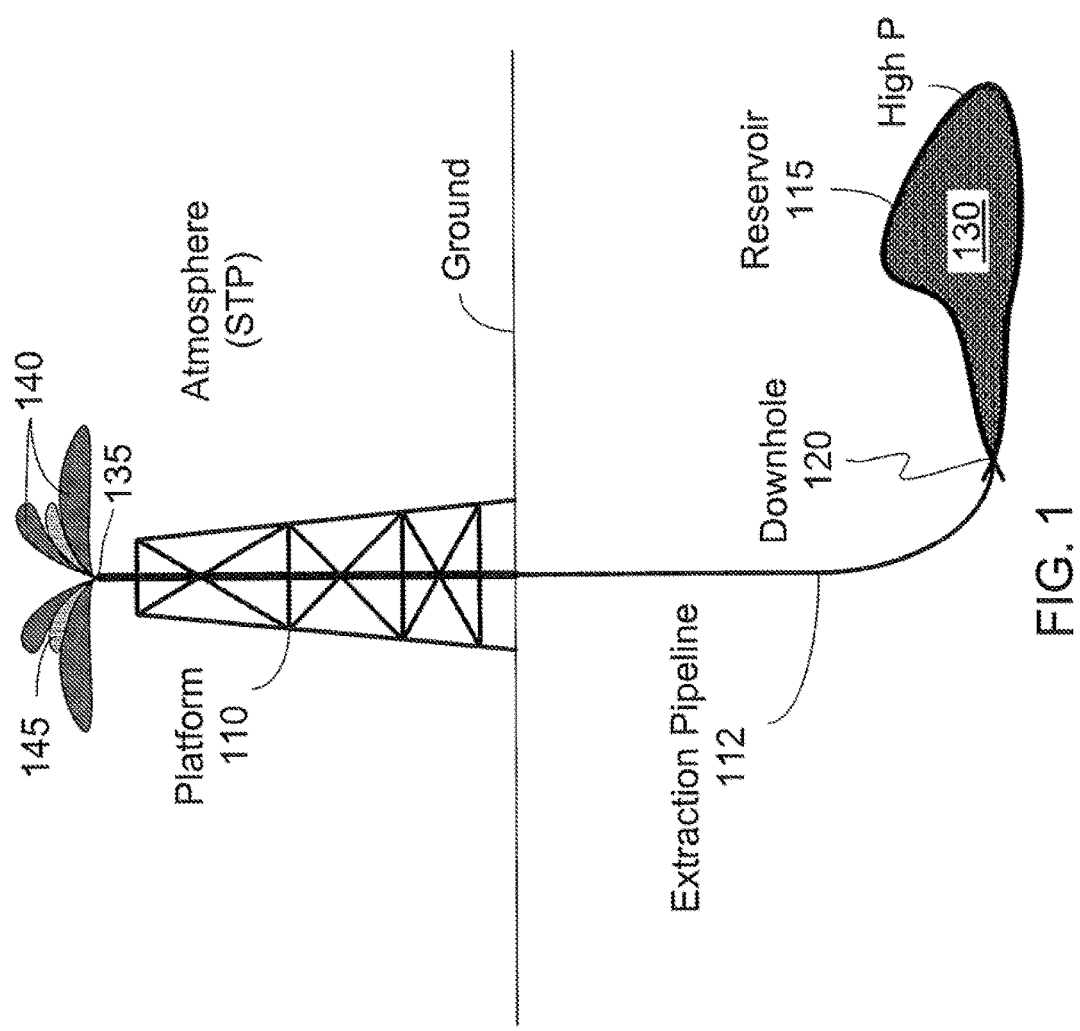
FIG. 1 shows an oil extraction platform according to some embodiments.

FIG. 1 shows oil extraction platform 110 according to some embodiments. Platform 110 is in an atmospheric environment at approximately STP conditions. STP conditions are 1 atm of pressure and 20° C. of temperature (about 68° F.). Platform 110 may include extraction pipeline 112 extending underground to downhole 120. Downhole 120 is the underground point where the pipeline makes contact with reservoir 115, which includes live crude oil 130. A mechanism that may include valves, pumps, and other components (not shown in FIG. 1) directs crude oil 130 to the surface and out of platform 110 through outlet 135.

Crude oil 130 is a liquid containing a mixture of hydrocarbons forming oil, and dissolved gases such as methane $CH_4$, carbon dioxide, $CO_2$, and others. The dissolved gases will form a gaseous phase at atmospheric conditions. Thus, when crude oil 130 is released into the atmosphere it contains two main phases, a liquid phase 140, which is the commonly known 'oil,' and a gas phase 145 containing natural gas, including methane and other gases.

Figure 2A:
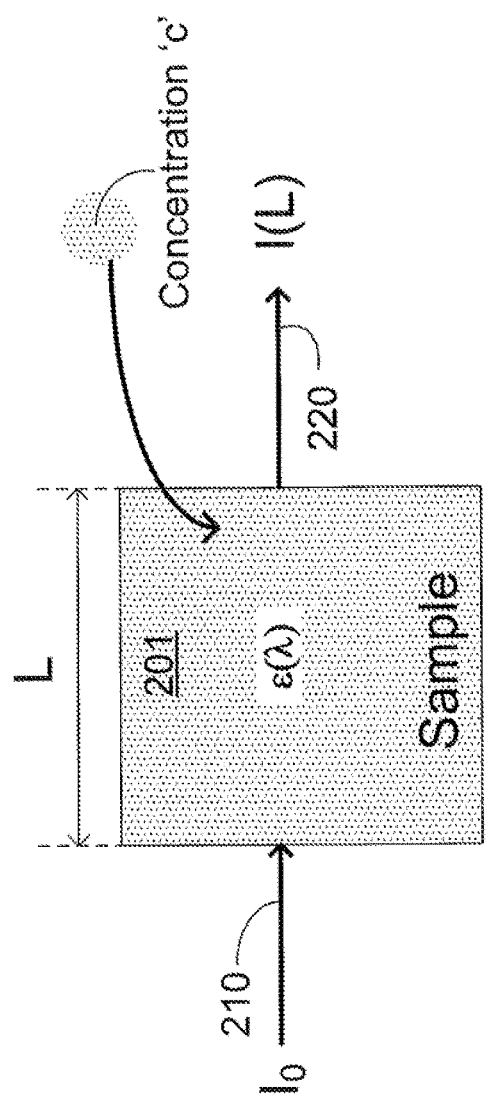
FIG. 2a. shows an absorption event for incoming light impinging on a sample and resulting in throughput light, according to some embodiments.

FIG. 2a shows an absorption event for incoming light 210 ($I_0$) impinging on sample 201 and resulting in throughput light 220 (I(L)), according to some embodiments. Sample 201 has a length, L, and contains an absorbing component with molar concentration 'c.' According to some embodiments disclosed herein, an apparatus for determining components in sample 201 may include a sample container having a fixed thickness, L. The optical design of the apparatus may be such that the thickness L corresponds to the optical path of input light 210 leading to throughput light 220.

Incoming light 210 and throughput light 220 include a plurality of components having different wavelengths, λ. In general, the wavelength components of incoming light 210 and throughput light 220 form a continuous spectrum. The ability of a component in sample 201 to absorb incoming light 210 is given by its molar absorptivity $\in(\lambda)$. Molar absorptivity, $\in(\lambda)$, depends on the wavelength component, λ, of incoming light 210. According to embodiments disclosed herein, absorbance measurements may be performed on samples 201 including methane gas $CH_4$ dissolved in liquid oil. Absorptivity, $\in(\lambda)$, may be related to a continuous spectral range having bandwidth Δλ and centered on wavelength λ. Such a continuous spectral range having bandwidth Δλ and wavelength λ, is referred to as spectroscopic envelope, and is described in detail with regard to FIG. 2b, below.

Figure 2B:
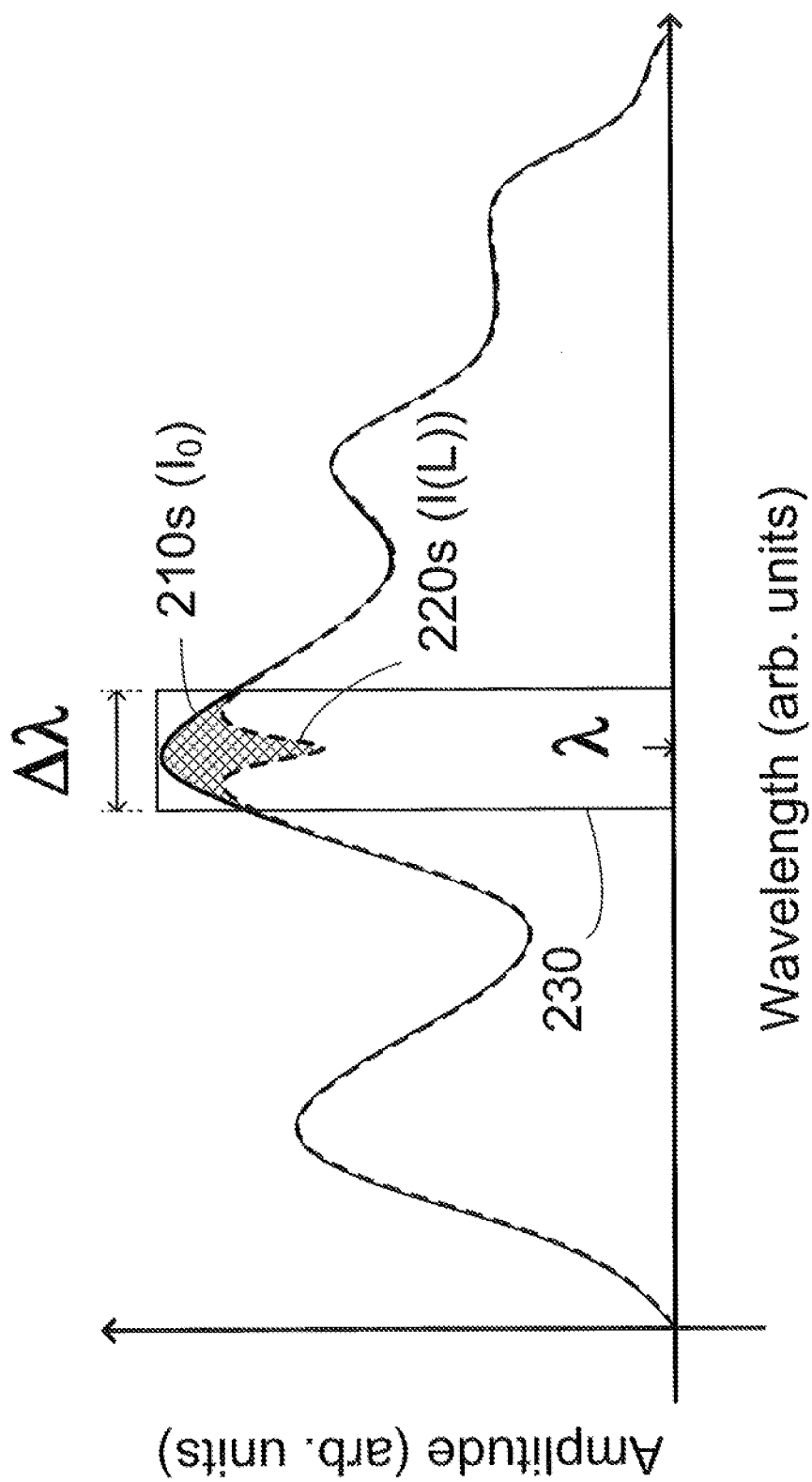

FIG. 2b shows spectroscopic envelope 230 for incoming light 210 and throughput light 220 according to embodiments consistent with FIG. 2a. FIG. 2b illustrates input light spectrum 210s and throughput light spectrum 220s. According to embodiments consistent with FIG. 2b, a portion of spectrum 210s is absorbed by the absorbing component in sample 201 and is not part of spectrum 220s. The absorbed portion is highlighted in FIG. 2b. Spectroscopic envelope 230 may have a spectral bandwidth including an absorbed portion, as illustrated in FIG. 2b. According to embodiments consistent with FIGS. 2a and 2b, a detector sensitive to light having components including spectroscopic envelope 230 may be used to measure input light 210 and throughput light 220. The relation between intensity $I_0$ of input 210 and intensity I(L) of throughput 220 may thus be given by Beer-Lambert (BL) absorption law, as follows:

$$I(L) = I_0 \cdot 10^{-\alpha(\lambda, L)}; \qquad (1)$$

Where no interference or scattering effects are considered. The exponential coefficient in Eq.(1), α, is the absorbance. The absorbance, α, is dependent on the molar absorptivity at spectroscopic envelope 230, $\in(\lambda)$ the molar concentration, c, and the length L of sample 201. In a linear approximation, the absorbance α may be modeled as:

$$\alpha(\lambda, L) = \in(\lambda) \cdot L \cdot c. \qquad (2)$$

Embodiments consistent with FIGS. 1, 2a and 2b, may use input light 210 ($I_0$) and a measurement of throughput light 220 (I(L)) to obtain absorbance, α, from Eqs.(1) and (2):

$$\alpha = -\text{Log}_{10}(I(L)/I_0); \qquad (3)$$

Absorbance data in the near infrared to mid-infrared wavelength domain may be modeled using Eqs. (1) and (2). Eqs.(1) and (2) provide an accurate model of sample 201 for values of $CH_4$ concentration below saturation. The saturation concentration for a given temperature (T) and pressure (P) condition is given by the maximum concentration of $CH_4$ that may be dissolved in the liquid sample before gas bubbles start forming in the mixture. For values of concentration higher than saturation, the appearance of bubbles may affect the collection of optical data due to interference effects and scattering. In the presence of interference and scattering, I(L) may not be properly described by Eq.(1).

Furthermore, Eq.(2) assumes that there is a linear relation between absorbance, α, and molar concentration 'c' of the absorbing component in the sample. The linear assumption is valid for relatively low values of the absorbance, α. Embodiments disclosed herein consistent with FIGS. 2a and 2b and the description in Eqs.(1), (2) and (3) have an absorbance, α, between 0 and 3.

According to embodiments disclosed herein, an apparatus using multiple spectroscopic envelopes to determine component concentrations may include an optical measurement of the ratio $I(L)/I_0$. Thus, using Eq. (1) with a knowledge of distance L, and absorptivity for spectroscopic envelope 230, $\in(\lambda)$, a concentration value may be obtained as:

$$c = -\frac{1}{\varepsilon(\lambda) \cdot L} \cdot \text{Log}(I(L)/I_0); \qquad (4)$$

Figure 2C:
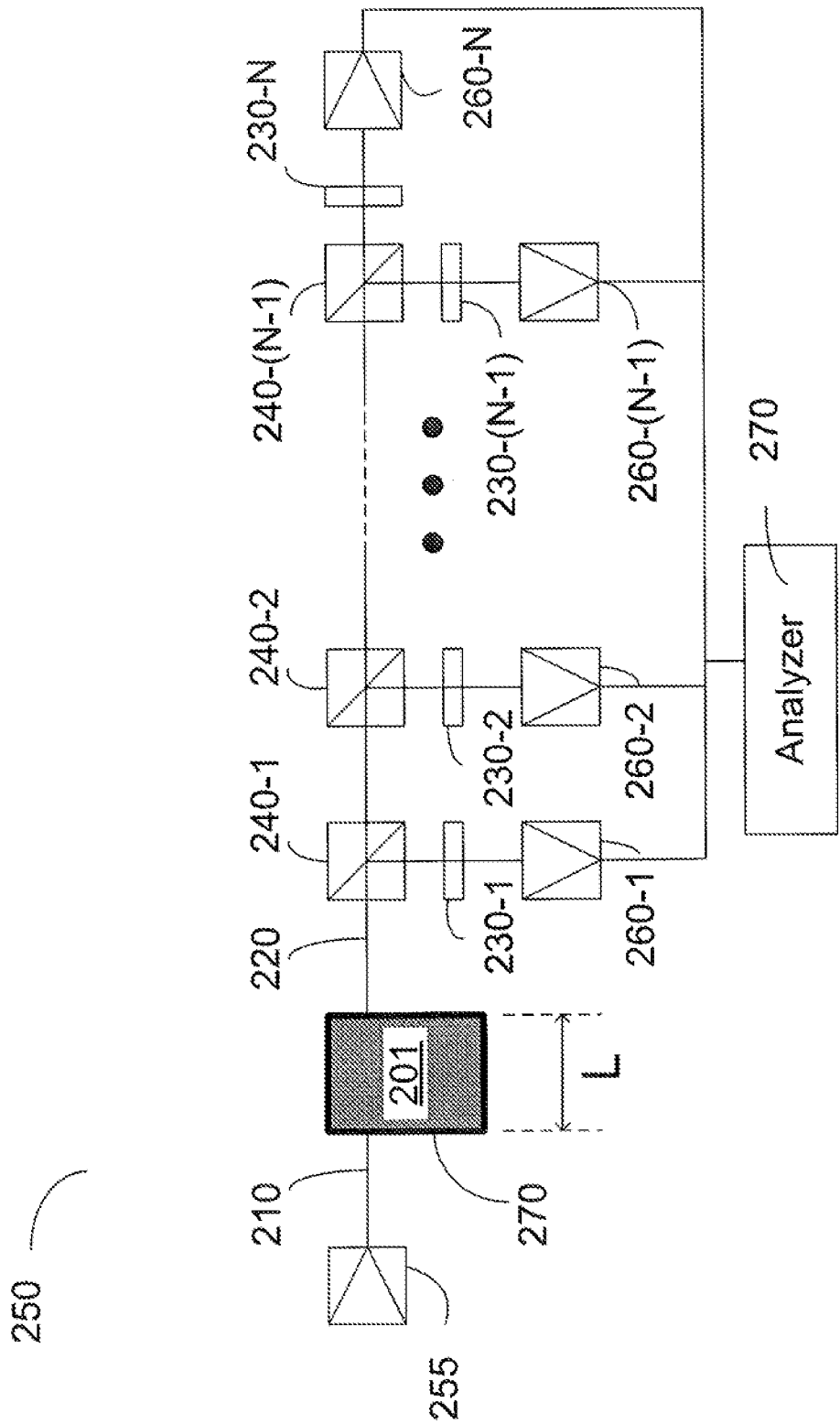
FIG. 2c shows a partial view of an apparatus for determining components in a sample, according to some embodiments.

FIG. 2c shows a partial view of apparatus 250 for determining components in sample 201, according to some embodiments. Apparatus 250 may include light source 255 to produce input light 210, and photo-detectors 260-1 through 260-N for measuring throughput light 220. Also included in apparatus 250 is sample container 270 having a thickness such that the optical path length of input light 210 through sample 201 is fixed to a distance L. According to embodiments consistent with FIG. 2c, a portion of throughput light 220 is coupled to each of the at least one photo-detectors 260 by optics 240-1 through 240-N. For example, optics 240-1 couples a portion of light 220 to photo-detector 260-1. In some embodiments such as illustrated in FIG. 2c, optics 240 may be a beam-splitter, so that element 240-(N−1) may couple a portion of light 220 to photo-detectors 260-(N−1) and 260-N. In some embodiments, optics 240-i, for i between 1 and N, may include more than one optical element, such as a mirror and a lens.

FIG. 2c also illustrates spectroscopic envelopes 230 through which select a portion of light 220 that is coupled to photo-detector 260. For example, envelope 230-1 selects a portion of light 220 that is coupled to detector 260-1, and envelope 230-N selects a portion of light 220 that is coupled to detector 260-N. The portion of light 220 selected by envelope 230-i may be the portion of spectrum 220s overlapping bandwidth $\Delta\lambda_i$ and centered on $\lambda_i$ (cf. FIG. 2b). In some embodiments consistent with FIG. 2c, envelopes 230-i may be band-pass filters, centered at wavelength $\lambda_i$ and having a bandwidth approximately equal to $\Delta\lambda_i$. For example, band pass filters 230-i may be thin film filters. In some embodiments, filters 230-i may all be included in a single element such as a tunable optical filter. A tunable optical filter is an optoelectronic device that provides a variable band-pass $\Delta\lambda_i$ at a desired center wavelength $\lambda_i$ by providing an electronic signal to an acousto-optic crystal.

Embodiments of apparatus 250 consistent with FIG. 2c may include a single photo-detector 260 coupled to spectroscopic envelopes 230-1 through 230-N. Also, some embodiments of apparatus 250 may include a single optics 240 having spectroscopic envelopes 230-1 through 230-N. In some embodiments, spectroscopic envelopes 230-1 through 230-N may be included as part of optics 240, such as a MOE.

Figure 2D:
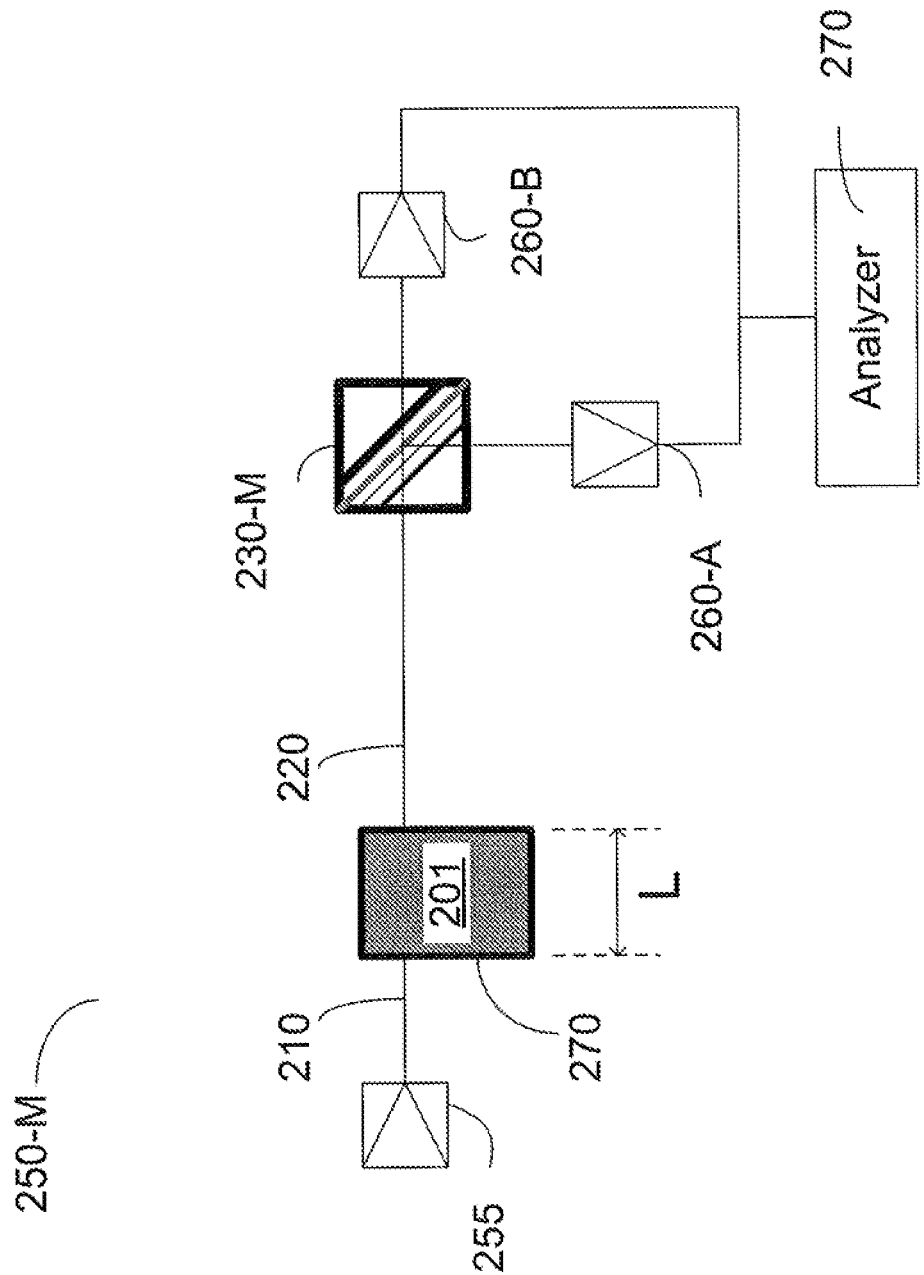
FIG. 2d shows a partial view of an apparatus for determining components in a sample using a Multivariate Optical Element (MOE), according to some embodiments.

FIG. 2d shows a partial view of apparatus 250-M for determining components in a sample using MOE 230-M, according to some embodiments. According to embodiments consistent with FIG. 2d, MOE 230-M may include spectroscopic envelopes 230-1 through 230-N in a single, multi-layered dielectric element. Apparatus 250-M may include detectors 260-A and 260-B. Detector 260-A measures light reflected from MOE 230-M, and detector 260-B measures light transmitted through MOE 230-M. By separately collecting the signals from detectors 260-A and 260-B, analyzer 270 may obtain an accurate value of the difference between spectra 210s and 220s (cf. FIG. 2b). Further, the use of MOE 230-M may enable the determination of the difference between spectra 210s and 220s in a plurality of spectroscopic envelopes 230-i. In some embodiments consistent with FIG. 2d, data for a plurality of spectral envelopes 230-i may be obtained in a single measurement.

Some embodiments of apparatus 250 consistent with FIG. 2c may include a dispersive element to physically separate different spectral components of light 220. Such dispersive element may include a prism or a diffraction grating, in some embodiments. In such embodiments, detectors 260-1 through 260-N may be included in an array of detectors, such as a CCD or a CMOS array. Further, in some embodiments, elements 240-i, 230-i, and 260-i may be included in a spectrometer having a diffraction grating and a CCD or CMOS detector array.

According to embodiments consistent with FIGS. 2c and 2d, detectors 260-1 through 260-N, and 260-A, B may be coupled to analyzer 270. Analyzer 270 processes the data provided by detectors 260-1 through 260-N, or 260-A and 260-B, to determine a concentration value for the absorbing component in sample 201.

Figure 3:
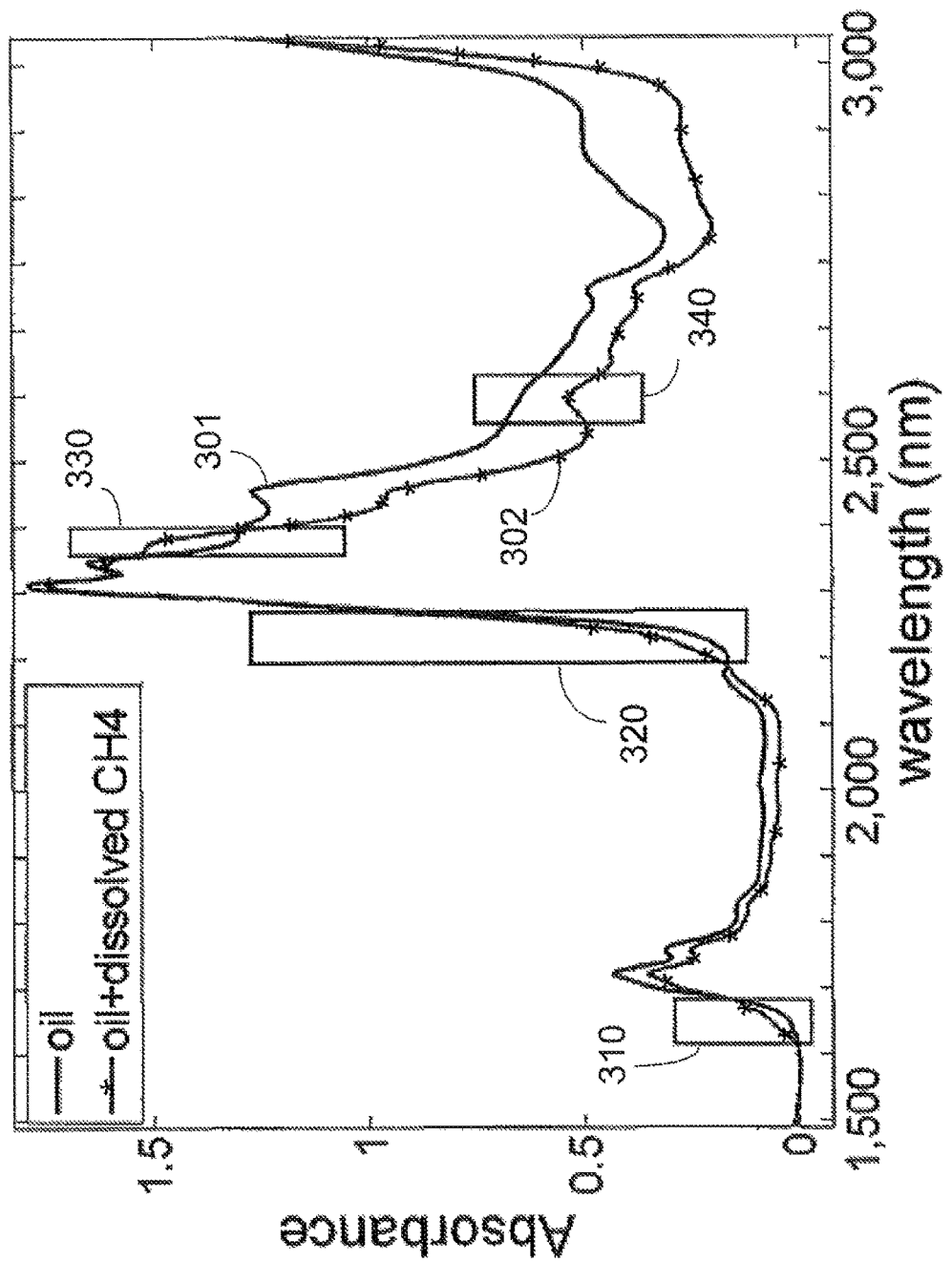
FIG. 3 shows absorbance spectra according to some embodiments.

FIG. 3 shows absorbance spectra 301 and 302 of oil samples, according to some embodiments. Absorbance spectra include arrays of values $\alpha(\lambda, L)$ as in Eq. (1) for a continuum of wavelengths $\lambda$, and a fixed sample length, L. Samples 301 and 302 may be liquid oil mixtures having different concentrations of hydrocarbons, including methane ($CH_4$). Samples 301 and 302 are similar in terms of their liquid hydrocarbon composition, having a difference in the amount of $CH_4$ dissolved in it. While sample 301 may contain zero moles of $CH_4$ dissolved in it, sample 302 may have certain amount, c, of $CH_4$ dissolved in it. For example, $CH_4$ concentration in sample 302 may be close to saturation. According to FIG. 3, spectroscopic envelopes 310, 320, 330 and 340 may be selected to obtain a value of 'c.' Each of the plurality of spectroscopic envelopes has a center wavelength $\lambda_i$, and a bandwidth, $\Delta\lambda_i$. In general, spectroscopic envelopes may have different bandwidths from one another ($\Delta\lambda_i \neq \Delta\lambda_j$ for $i \neq j$). In some embodiments, spectroscopic envelopes are non-overlapping in wavelength. Thus, the spectral range covered may be different for each spectroscopic envelope. Some embodiments may include overlapping spectral ranges for two or more spectroscopic envelopes.

Using Eq. (1) for each spectroscopic envelope 'i,' where 'i' may correspond to any one of envelopes 310, 320, 330 and 340 may result in a concentration measurement:

$$c = -\frac{1}{\varepsilon_i(\lambda_i) \cdot L} \cdot \mathrm{Log}(I_i(L)/I_{0i}); \tag{5}$$

According to FIG. 3, spectroscopic envelopes covering the wavelength range from 1500 nm to 3000 nm may be used. In embodiments consistent with FIG. 3, spectroscopic envelopes 310, 320, 330, and 340 may correspond to Alkane absorption bands. Alkanes are saturated hydrocarbon compounds having only single bonds between the atoms. Alkane envelope 310 is located between 1620 and 1700 nm. Envelope 320 is located between 2190 and 2270 nm. Envelope 330 is located between 2360 and 2400 nm. And envelope 340 is located between 2530 and 2650 nm. The dynamic range may cover a wavelength range from 1500 to 3000 nm. Other spectroscopic envelopes within the 1500-3000 nm range may be selected according to the absorbance spectra shown in FIG. 3. The criteria to select a specific spectroscopic envelope vary according to the application, availability and cost of filtering elements covering the desired envelope. For example, the wavelength region from 2700-2900 nm shows a large difference between spectra 301 and 302. It seems attractive to use a spectroscopic envelope covering the region from 2700-2900 nm. Considerations such as availability of high quality optical filters in the 2700-2900 nm region may be included for the use of such envelopes.

Another factor to consider in the selection of spectroscopic envelopes is the presence of interfering absorption bands in the selected envelope. Interfering absorption bands may come from different components in the sample. For example, strong absorption bands from $CO_2$ and $H_2O$ (water) are known to exist in the spectral range from 1500 to 3000 nm.

The use of multiple spectroscopic envelopes, each having absorptivity $\varepsilon_i(\lambda_i)$, renders multiple values of 'c' for a single component. These multiple values of 'c' may be compared to one another, providing a more accurate concentration measurement. For example, multiple values of 'c' obtained through Eq.(4) may be averaged and the standard deviation may provide an accurate estimate of an error measurement. This may be desirable in situations where a spectroscopic envelope alone may be associated with a relatively high absorptivity $\varepsilon_i(\lambda_i)$. In such situations, the high absorptivity in envelope 'i' may be leveraged by using a different envelope 'j' having a relatively low absorptivity $\varepsilon_j(\lambda_j) \ll \varepsilon_i(\lambda_i)$, so that the linearity of Eq.(2) is maintained.

In some embodiments consistent with FIG. 3, a method and apparatus to determine components in a sample may include an envelope 'j' having low absorptivity $\varepsilon_j(\lambda_j)$, and envelope 'i' having a higher absorptivity $\varepsilon_i(\lambda_i)$ such that $\varepsilon_j(\lambda_j) \ll \varepsilon_i(\lambda_i)$. Such embodiments may perform accurately for samples having very low concentrations 'c' of the absorbing component through the absorbance provided by envelope 'i.' In the case of samples having very low values of 'c,' the linearity of Eq.(2) may be valid, but the level of absorption may be difficult to measure using envelope T only. Embodiments having envelopes 'j' and 'i' may also perform accurately for samples having high concentrations 'c' of the absorbing component. In such samples, while the linearity of Eq.(2) may be compromised for envelope 'i,' the linear hypothesis may be highly accurate for envelope 'j.' The result is a broad dynamic range of operation and applicability of the method and apparatus to determine components in a sample.

Embodiments consistent with the concept of FIG. 3, using multiple spectroscopic envelopes 'i,' may reduce the sensitivity of the system to noise. For example, flickering noise may occur in light 210 due to instrument effects in the light source used for measurement. Other effects may occur in the optical transmission line between a light source and sample 201. The result of these noise effects may be that input light 210 changes in intensity by the same factor for all envelopes 230:

$$I_{0i}^{new} = \kappa \cdot I_{0i}^{old}; \tag{6.1}$$

$$I_{0j}^{new} = \kappa \cdot I_{0j}^{old}. \tag{6.2}$$

By using Eq.(4) for the two spectroscopic envelopes 'i' and 'j' in the form $$\epsilon_i(\lambda_i) \cdot L \cdot c = -\text{Log}_{10}(I_i/I_{0i}^{new}); \quad (7.1)$$

$$\epsilon_j(\lambda_j) \cdot L \cdot c = -\text{Log}_{10}(I_j/I_{0j}^{new}). \quad (7.2)$$

Subtracting Eq. (7.1) and Eq. (7.2) and using Eqs. (6.1) and (6.2) one arrives at $$c = \frac{\text{Log}_{10}(I_j \cdot I_{0i}^{new}/(I_i \cdot I_{0j}^{new}))}{L \cdot (\epsilon_i(\lambda_i) - \epsilon(\lambda_j))} = \frac{\text{Log}_{10}(I_j \cdot I_{0i}^{old}/(I_i \cdot I_{0j}^{old}))}{L \cdot (\epsilon_i(\lambda_i) - \epsilon(\lambda_j))}; \quad (8)$$

Thus, according to embodiments consistent with FIG. 3, Eq.(8) may be used to measure a value of concentration 'c' that is independent of flickering noise or other factors affecting the intensity of input light 210 homogeneously (i.e. an approximately equal effect for all wavelengths).

Embodiments consistent with the concept of FIG. 3 using 'N' multiple spectroscopic envelopes 'i' may be used in combination with multivariate linear regression techniques. In such embodiments, a plurality of 'M' absorbing components in sample 201 may be measured using N multiple spectroscopic envelopes. A vector c may be formed including a plurality of 'M' concentrations '$c_i$' for each of the absorbing components in sample 201. In such embodiments, vector a may be formed including a plurality of 'N' absorbances $\alpha_j$. Each entry 'j' in vector a may be associated to a spectroscopic envelope centered on wavelength According to some embodiments using a linear approximation, vector a may be obtained from a generalization of Eq.(2), above:

$$\alpha = L \cdot E \cdot c. \quad (9)$$

In Eq.(9), E is an N×M matrix producing an N-dimensional vector (proportional to a) from an M-dimensional vector (c). Matrix E includes elements '$e_{ij}$' in row 'i' and column 'j.' Element '$e_{ij}$' in matrix E may be the contribution of component having concentration '$c_j$' to absorbance '$a_i$.' Thus, matrix E includes information not specific to sample 201 and may be calibrated prior to measurement. Vector a may be measured using input light 210 and throughput light 220. With a knowledge of $\alpha$ and E, vector c may be obtained by solving Eq.(9) using linear regression techniques. The concentrations of the 'M' absorbing components in sample 201, c, may thus be obtained.

In some embodiments, numbers N and M may be the same, so that inversion of matrix E in Eq.(7) is straightforward. In some embodiments, N and M may be different, and diagonalization techniques may be used to solve Eq.(9) for vector c. Techniques for solving Eq.(9) may be obvious to one of regular skill in the art of linear algebra and multivariate regression algorithms.

Embodiments consistent with the concept of FIG. 3 using multiple spectroscopic envelopes 'i' may also be used to perform a baseline extraction from absorbance spectra 301 and 302. Baseline extraction will be described in detail with reference to FIG. 4, as follows.

Figure 4:
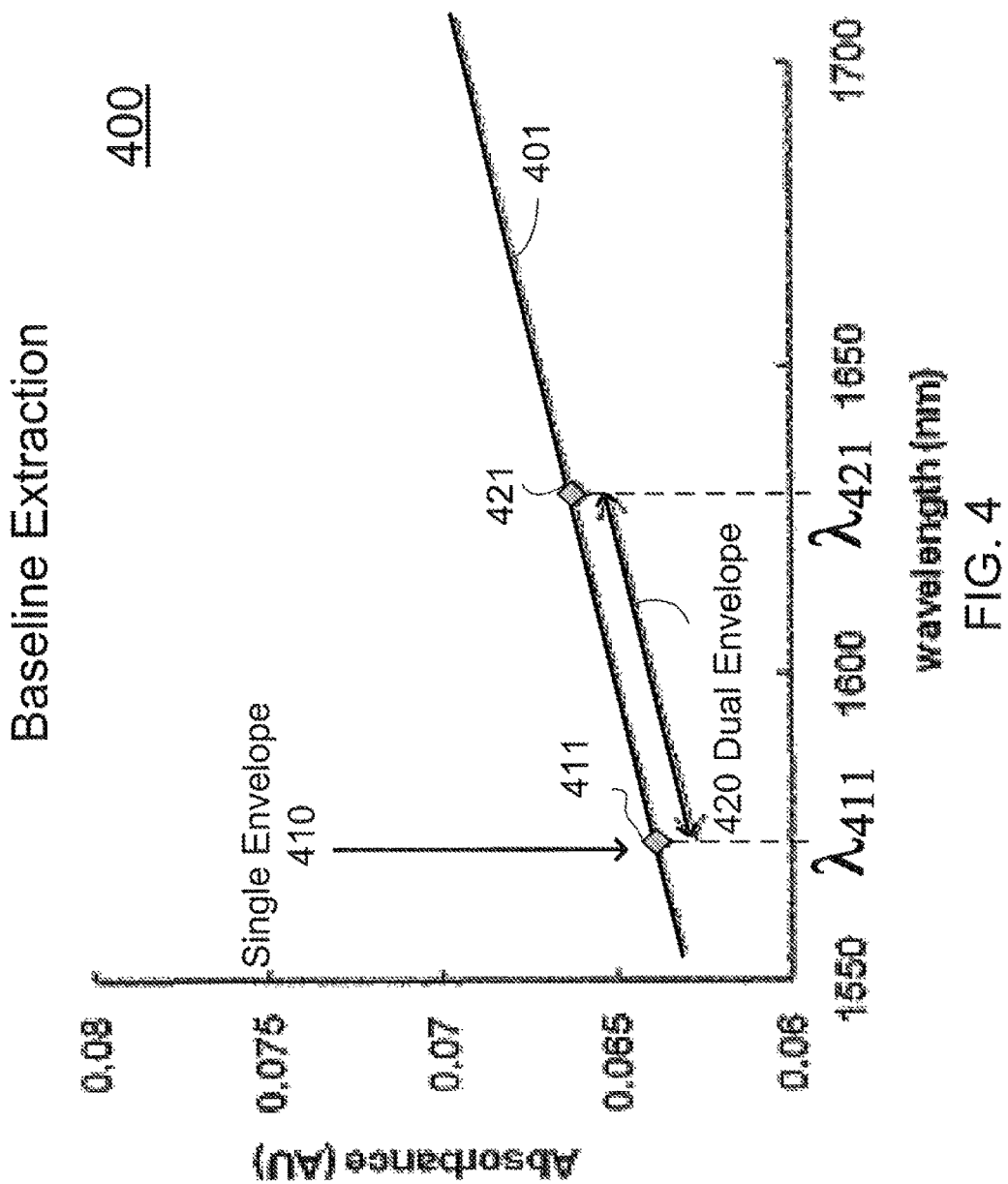
FIG. 4 shows a baseline extraction using multiple spectroscopic envelopes according to some embodiments.

FIG. 4 shows baseline extraction 400 using multiple spectroscopic envelopes according to some embodiments. In some embodiments consistent with FIG. 4 absorbance baseline 401 may be a linear function of wavelength, $\lambda$. Baseline 401 is an 'absorbance' measurement that may be obtained by plotting $\text{Log}_{10}(I(L)/I_0)$ for different wavelengths $\lambda$ having a homogeneous sample 201 with no absorbing components. In some embodiments, baseline 401 may be obtained by collecting light 220 from light 210 passing through a 'blank' sample 201. For example, a blank sample may be a sample having thickness L and a homogeneous index of refraction '$n_b$' similar to the real part of the index of refraction '$n_s$' of the sample of interest. In some embodiments the sample of interest is live crude oil.

According to embodiments consistent with FIGS. 3 and 4, the effect of baseline 401 in the overall absorbance spectrum may be very small. This may be seen by comparing the ordinate values in FIGS. 3 and 4. Nonetheless, baseline 401 may have a deleterious effect in the accuracy of concentration measurements, and some embodiments may benefit from its extraction from absorbance data.

As shown in FIG. 1, a model and apparatus to determine components of a sample that uses a single envelope 410 may not be able to find baseline 401. Even if baseline 401 is only a straight line having a slope, baseline measurement 411 using a blank sample as described above at wavelength $\lambda_{411}$ only provides one point in baseline 401. As illustrated in FIG. 4, some embodiments of baseline extraction 400 may include measurement 421 using a second spectroscopic envelope centered at wavelength $\lambda_{421}$. In such embodiments baseline 401 may be completely determined with data points 411 and 421.

Further extensions of the method and apparatus for baseline extraction consistent with the concept illustrated in FIG. 4 are obvious to one of regular skill in the art. For example, using a third spectroscopic envelope may enable the removal of a baseline having a second degree dependence on wavelength, $\lambda$. More generally, having a number 'N' of spectroscopic envelopes may enable baseline extraction 400 for a baseline including a polynomial of 'N−1' degree.

Figure 5:
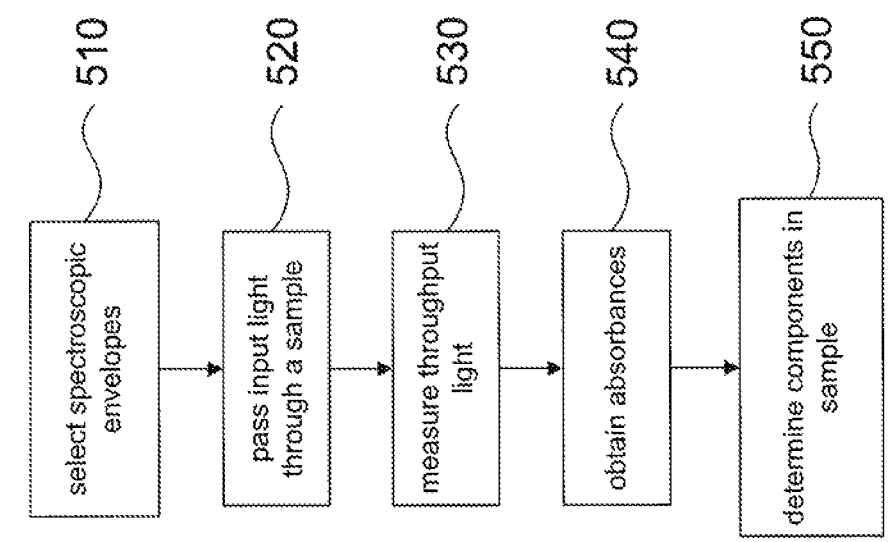
FIG. 5 shows a flow chart for a method of using multiple spectroscopic envelopes to determine components in a sample, according to some embodiments.

FIG. 5 shows a flow chart for method 500 for using multiple spectroscopic envelopes to determine components in a sample, according to some embodiments.

In step 510 a plurality 'N' of spectroscopic envelopes is selected within a wavelength region of interest. The value of N may be 1, or any number greater than 1. In some embodiments, a lower number of spectroscopic elements may be preferred for simplicity of operation and cost reduction. The selection of spectroscopic envelopes is made according to the component that is desired to be measured in sample 201. For example, in embodiments of method 500 used for measuring GOR, spectroscopic envelopes may include a wavelength region between 1500 and 3000 nm. Furthermore, in embodiments used for measuring GOR, at least one spectroscopic envelope may include an absorption band for methane ($CH_4$).

In step 520, input light 210 is passed through sample 201, having a thickness, L. Input light 210 may be selected to have a spectral composition 210s which allows a substantial amount of light 210 to be transmitted through sample 201 (cf. FIG. 1). Also, spectrum 210s may be such that a portion of the spectrum is selectively absorbed by a component in sample 201. In some embodiments of method 500 spectrum 210s is such that different portions in spectrum 210s may be absorbed by a component in sample 201. Furthermore, in some embodiments there may be a plurality of components in sample 201 absorbing a plurality of portions in spectrum 210s. Input light 210 may also be selected according to availability of efficient photo-detectors in a spectral range including spectrum 210s.

In step 530, throughput light 220 is measured using a photo-detector. Throughput 220 is measured for each spectroscopic envelope 230 selected. In some embodiments, throughput 220 for each envelope 230 is measured independently, using a single photo-detector. In some embodiments, throughput 220 may be measured simultaneously for all envelopes 230, using an array of photo-detectors coupled to a spectrometer. Some embodiments of method 500 consistent with FIGS. 1 through 5 may perform step 530 using a MOE. In such embodiments, throughput light 220 may be directed onto a MOE. Light 220 transmitted from the MOE may be measured using a photo-detector. Light 220 reflected from the MOE may be measured using a photo-detector. According to some embodiments, a MOE may be designed such that a difference between the transmission and reflection measurement in the absence of sample 201 is proportional to the sum of the components of a pre-selected vector. In some embodiments, the preselected vector may be obtained by multiplying a reference spectrum with the solution to a multivariate linear regression problem. The transmission and reflection measurement of light 220 from the MOE in the presence of sample 201 may then be used to determine a component concentration as described in detail below.

According to embodiments consistent with FIGS. 1 through 5, a MOE may include a multi-layered thin film optical element such as described in U.S. patent application Ser. No. 11/684,779 entitled "Thin Film Interference Filter and Bootstrap Method for Interference Filter Thin Film Deposition Process Control," by Michael L. Myrick et al. The use of a MOE for determining components in a sample is described in U.S. patent application Ser. No. 12/295,631, entitled "Data Validation and Classification in Optical Analysis Systems," by Michael L. Myrick et al.

Some embodiments of a method consistent with FIG. 5 may include step 540 to obtain at least one absorbance value from the measurement of throughput light 220. In some embodiments, step 540 is performed by using Eq.(3), above. Some embodiments consistent with FIGS. 1 through 5 may perform step 540 by using a linear approximation to Eq.(3) in the limit of low absorbances. In such embodiments, an absorbance for input 210 and throughput 220 (I(L)) may be approximated as $$\alpha = -\frac{I(L) - I_0}{I_0}; \quad (10)$$

In step 540, an absorbance value may be obtained for each of the spectroscopic envelopes 230 selected in step 510.

In step 550 a component in sample 201 is determined. In some embodiments, the absorbance value obtained in step 540 above may be used in a linear model such as described by Eq.(2) or Eq. (9). In such embodiments, step 550 may include obtaining a concentration value for the component in sample 201. Embodiments of method 500 consistent with FIGS. 1 through 5 using a MOE may perform step 550 with a solution of a linear regression problem for determining a component in a sample. In such embodiments, the solution for a linear regression problem may be a linear equation. The linear equation may relate the difference in transmission and reflection of light 220 from a MOE, to a concentration value for an absorbing component of sample 201. The linear relation may include a proportionality factor, β, and an offset value, γ. The values of β and γ may be pre-determined by a calibration process.

In some embodiments of step 550, determining a component in sample 201 may include obtaining concentration values for a plurality of components in sample 201.

Embodiments described herein are exemplary only. One skilled in the art may recognize various alternative embodiments from those specifically disclosed. Those alternative embodiments are also intended to be within the scope of this disclosure. As such, the embodiments are limited only by the following claims.

What is claimed is:

1. A method of using spectroscopic envelopes for determining components in a sample, the method comprising the steps of: selecting a plurality of spectroscopic envelopes that overlap at least two absorption bands of a single absorbing component, the at least two absorption bands having different absorptivities for the single absorbing component; passing input light through the sample comprising the single absorbing component; measuring throughput light from the sample with a photo-detector; and using the different absorptivities of the at least two absorption bands, determining the concentration of the single absorbing component in the sample.

2. The method of claim 1, wherein the sample is crude oil in the downhole of an extraction platform and the single absorbing component is methane.

3. The method of claim 2 wherein the concentration measurement is related to a gas-oil-ratio ("GOR") in crude oil at an outlet of the extraction platform.

4. The method of claim 1 wherein determining the concentration of the single absorbing component comprises a baseline extraction step.

5. The method of claim 4 wherein the baseline extraction step removes a linear baseline from a spectrum.

6. The method of claim 4 wherein the baseline extraction step removes a polynomial baseline from a spectrum, where the polynomial has a degree greater than or equal to one.

7. The method of claim 1, wherein determining the concentration of the absorbing component comprises:
obtaining a first absorptivity for the single absorbing component;
obtaining a second absorptivity, lower than the first absorptivity, for the single absorbing component; and
determining the concentration of the single absorbing component using the first and second absorptivity.

8. The method of claim 1, wherein determining the concentration of the absorbing component comprises averaging a plurality of absorptivities for the single absorbing component.

9. An apparatus for determining components in a sample, the apparatus comprising:
an input light source having a spectrum;
a sample container having a fixed optical path-length;
wherein the input light passes through a sample in the sample container forming a throughput light, the sample having at least one absorbing component;
a plurality of pre-selected spectroscopic envelopes to select spectral portions of the throughput light from the sample;
at least one photo-detector to measure the throughput light selected by the spectroscopic envelopes; and
an analyzer to use the measurement from the photo-detectors to determine the concentration of the at least one absorbing component in the sample,
wherein the spectroscopic envelopes are selected to overlap at least two absorption bands having different absorptivities for a single absorbing component, the different absorptivities of the at least two absorption bands being used to determine the concentration of the single absorbing component in the sample.

10. The apparatus of claim 9 wherein the plurality of pre-selected spectroscopic envelopes comprises portions of the Alkane absorption spectra.

11. The apparatus of claim 9 wherein at least two of the plurality of pre-selected spectroscopic envelopes have spectral portions overlapping each other.

12. The apparatus of claim 9 wherein the plurality of pre-selected spectroscopic envelopes comprises optical absorption filters.

13. The apparatus of claim 9 wherein the plurality of pre-selected spectroscopic envelopes comprises optical interference filters.

14. The apparatus of claim 9 wherein the plurality of pre-selected spectroscopic envelopes comprises a multivariate optical element ("MOE").

15. The apparatus of claim 9 wherein the plurality of pre-selected spectroscopic envelopes include the 1500 nm-3000 nm spectral range.

16. The apparatus of claim 9 wherein the plurality of pre-selected spectroscopic envelopes include an absorption band of methane.

17. The apparatus of claim 9 wherein the plurality of pre-selected spectroscopic envelopes include an absorption band of carbon dioxide.

18. The apparatus of claim 9 wherein the plurality of pre-selected spectroscopic envelopes include an absorption band of water.

19. The apparatus of claim 9 wherein the plurality of pre-selected spectroscopic envelopes include an absorption band of hydrogen sulfide ($H_2S$).

* * * * *